United States Patent
Buchwald et al.

(10) Patent No.: US 6,806,091 B1
(45) Date of Patent: Oct. 19, 2004

(54) METHOD AND APPARATUS FOR DETERMINING BLOOD OXYGEN TRANSPORT

(76) Inventors: Henry Buchwald, 6808 Margaret's La., Edina, MN (US) 55439; Hector J. Menchaca, 13834 Essex Trail, Apple Valley, MN (US) 55124; Van Michalek, 2839 Aglen Ave. North, Roseville, MN (US) 55113; Thomas J. O'Dea, 925 Arbogast St., Shoreview, MN (US) 55120; Thomas D. Rohde, 702 Third Ave. SE., Minneapolis, MN (US) 55414

( * ) Notice: Subject to any disclaimer, the term of this patent is extended or adjusted under 35 U.S.C. 154(b) by 0 days.

(21) Appl. No.: 09/600,094
(22) PCT Filed: Jan. 12, 1999
(86) PCT No.: PCT/US99/00613
 § 371 (c)(1),
 (2), (4) Date: Aug. 22, 2000
(87) PCT Pub. No.: WO99/35492
 PCT Pub. Date: Jul. 15, 1999

(51) Int. Cl.$^7$ .................. G01N 33/50; G01N 33/92
(52) U.S. Cl. ............... 436/136; 436/63; 436/68; 436/71; 436/127; 436/164; 436/167; 436/168; 422/68.1; 422/73; 422/82.05; 422/82.09; 422/83; 422/88; 435/2
(58) Field of Search ................. 436/63, 66, 68, 436/71, 127, 136, 138, 164, 167, 168, 172, 181, 82.08; 422/68.1, 73, 82.05, 82.09, 83, 88, 99; 435/2

(56) References Cited

U.S. PATENT DOCUMENTS

| 3,647,299 A | 3/1972 | Lavallee |
| 3,779,708 A | 12/1973 | Runck et al. |
| 4,013,417 A | 3/1977 | Raffaele ................ 422/67 |
| 4,120,658 A | 10/1978 | Bruttig |
| 4,133,874 A | 1/1979 | Miller et al. ............ 424/450 |
| 4,209,300 A | 6/1980 | Thibault ................ 436/66 |
| 5,604,105 A | 2/1997 | Jackowski |
| 5,686,300 A | 11/1997 | Berndt ................ 435/287.5 |
| 6,037,181 A * | 3/2000 | Buchwald et al. ........ 422/68.1 |

FOREIGN PATENT DOCUMENTS

| EP | 0 240 742 A2 | 10/1987 |
| JP | 01088340 | 4/1989 |
| RU | 2073485 | 2/1997 |
| SU | 1739295 | 6/1992 |
| WO | WO 96/03655 | 2/1996 |

OTHER PUBLICATIONS

Anderson, H.V., et al., "Coronary artery flow monitoring coronary interventions," *European Heart Journal (Supplement J)* 16:71–73 (1995).

Clark, Jr., A. et al. "Oxygen Delivery From Red Cells," *Biophysical Journal*, 47:171–181 (Feb. 1985).

(List continued on next page.)

Primary Examiner—Maureen M. Wallenhorst
(74) Attorney, Agent, or Firm—Merchant & Gould P.C.

(57) ABSTRACT

The present invention relates to a method and apparatus for determining blood oxygen transport, and to measure lipid levels by correlating these levels with the rate at which oxygen diffuses through the red blood cell membrane.

42 Claims, 7 Drawing Sheets

OTHER PUBLICATIONS

Di Mario, C. et al., "Principles of interpretation of coronary velocity and pressure tracings," *European Heart Journal, (Supplement J)*, 16:53–59.

Guyton, A.C., *Textbook of Medical Physiology*—eighth edition; sections on coronary blood flow; diffusion, oxygen capacity of blood, pp. 186, 237, 43–44; 434–439 (WB Saunders, Philadelphia, Pa. 1991).

Huxley, V. H., et al., "Effect of Diffusion Boundary Layers on the Initial Uptake of $O_2$ by Red Cells. Theory versus Experiment," *Microvascular Research*, 26:89–107 (1983).

Mendelson, Y. et al., "In–vitro Evaluation of a Dual Oxygen Saturation/Hematocrit Intravascular Fiberoptic Catheter," *Biomedical Instrumentation & Technology*, 24:199–206 (May/Jun. 1990).

Page, T. C. et al., "Chapter 9—Experimental Stimulation of Oxygen Transport in Microvessels," pp. 132–145 (undated).

Page, T. C. et al., "Oxygen Transport by Erythrocyte/Hemoglobin Solution Mixtures in an in Vitro Capillary as a Model of Hemoglobin–Based Oxygen Carrier Performance," *Microvascular Research*, 55:54–64 (1998).

Popel, A.S., "Theory of Oxygen Transport to Tissue," *Critical Reviews in Biomedical Engineering*, 17(3):257–321 (1989).

Steinbach, J. H. et al., "High Blood Cholesterol Reduces in Vitro Blood Oxygen Delivery," *Journal of Surgical Research*, 16:134–139 (1974).

Tsai, A. G. et al., "Chapter 8—Microvascular Oxygen Distribution. Effects Due to Free Hemoglobin in Plasma," pp. 124–131 (undated).

Villars, F.M. et al., *Physics with Illustrative Examples from Medicine and Biology*, vol. 2. Statistical Physics; sections on the diffusion equation; Particle Conservation and Fick's Law; Transport of Water and Solute Across Biological Membranes, pp. 2–46 to 2–47; 2–66 to 2–79; 2–81 to 2–83; 2–92 to 2–97; 2–106; 2–192 to 2–203 (Addison–Wesley, Reading, Mass., 1974).

Stathopoulos, N. et al., "Oxygen Transport Studies of Normal and Sickle Red Cell Suspensions in Artificial Capillaries", *Microvascular Research*, vol. 34, 1 pg., Abstract only (Sep. 1987).

Weatherall, D. et al., "Red Cells I: Inherited Anaemias", *The Lancet*, vol. 355, pp. 1169–1175 (Apr. 1, 2000).

* cited by examiner

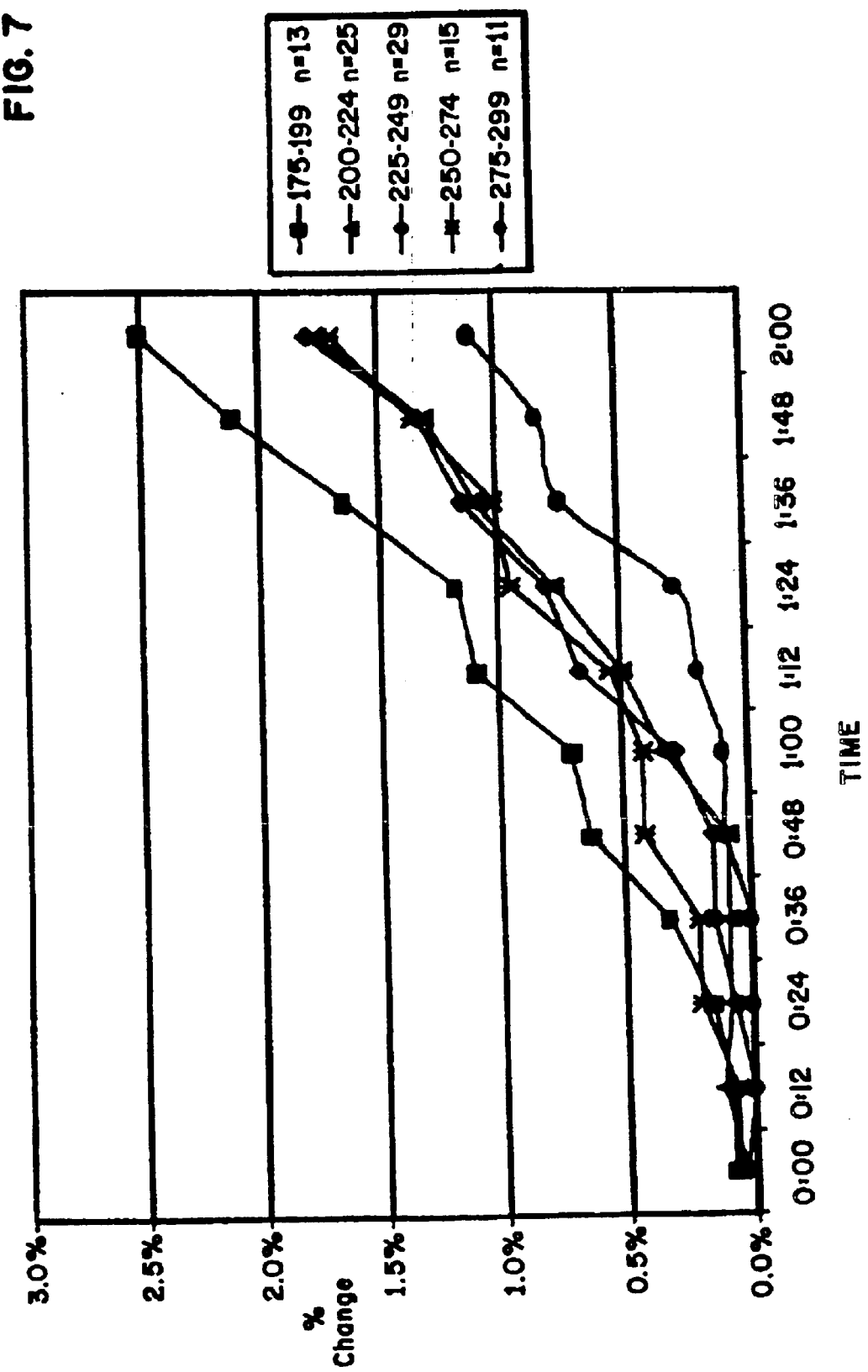

METHOD AND APPARATUS FOR DETERMINING BLOOD OXYGEN TRANSPORT

BACKGROUND OF THE INVENTION

The relationship between elevated blood lipids, particularly cholesterol (and especially low-density-lipoprotein cholesterol) and atherosclerosis has been known for many years. More recently, reduction of LDL cholesterol by means of surgery or drugs has been shown to reduce the risk of coronary heart disease. However, the reduction of cardiac events achieved by cholesterol lowering does not correlate well with the relatively small amount of physical regression in the amount of atherosclerotic plaque seen in the coronary arteries following treatment. In addition, relief of angina pectoris (ischemic chest pain) often occurs in a matter of weeks following cholesterol lowering; whereas, documentable changes in the inside diameters of coronary arteries may take years to occur, if they occur at all. The pain associated with angina pectoris is attributable primarily to lactic acid produced when heart muscle cell metabolism occurs in the absence of oxygen. Coronary artery narrowing can limit the amount of blood-transported oxygen that reaches the heart muscle tissue, but, the above observation suggests oxygenation of heart muscle tissue can be improved without increasing blood flow through the coronary vessels.

The way in which changes in blood lipids, such as cholesterol might affect oxygen delivery to heart muscle tissue has remained unclear. There is abundant oxygen in blood. In fact, oxygenated (arterial) blood contains approximately as many molecules of oxygen per 1000 mL as are found in 200 mL of oxygen gas. Almost all (98–99%) of this oxygen is bound to hemoglobin molecules within the red blood cells; the remainder is physically dissolved in plasma and intracellular red blood cell fluid. For oxygen to reach tissues, such as cardiac muscle tissue, oxygen must be released from hemoglobin and then diffuse across the red blood cell membrane into the plasma and from there into tissues. The movement of oxygen across the red blood cell membrane occurs by passive diffusion and is governed by concentration gradients, there is no active membrane transport system for oxygen. Furthermore, the composition of a subject's red blood cell membrane changes with changes in the subject's lipid status. Therefore, the red blood cell membrane, the immediate surroundings of the red blood cell (the boundary layer), or the contours of the red blood cell membrane can be a significant barrier to release of oxygen into tissue such as cardiac muscle tissue.

What is needed is a method and apparatus to assess the significance of the red blood cell membrane, the immediate surroundings of the red blood cell (the boundary layer), or the contours of the red blood cell membrane as a hindrance to oxygen transfer from blood to tissues, such as cardiac muscle tissue. Such a method and apparatus would provide a new way to assess heart and circulatory disorders related to oxygen transport, such as angina pectoris; a new way to measure, and to assess the impact of, factors that affect oxygen transport from a red blood cell, such as a patient's blood lipid levels; and a new way to monitor the effectiveness of lipid-lowering therapies or therapies for improving oxygen transport.

SUMMARY OF THE INVENTION

The present invention relates to an apparatus and method for determining the rate at which oxygen crosses the red blood cell membrane. The apparatus and method provide a way to assess heart and circulatory disorders related to oxygen transport. Advantageously, the apparatus and method of the invention can be used to assess a patient's susceptibility to angina pectoris, to determine a patient's blood lipid levels, to measure factors that affect oxygen transport from a red blood cell, and a new way to monitor the effectiveness of lipid-lowering therapy or therapy for improving oxygen transport.

The present method of measures a rate or rates of oxygen diffusion across a red blood cell membrane from the patient. Advantageously, red blood cell samples are standardized to generally uniform conditions of gas content by exposing the red blood cell to oxygen and exposing the red blood cell to an environment depleted of oxygen as part of the measurement process. Preferably, the rate at which oxygen moves across the red blood cell membrane or its boundary layer is determined by monitoring either a blood plasma level of oxygen, a level of oxygen bound to hemoglobin, or both.

The present method of determining a patient's blood lipid level, and its impact, includes measuring a rate or rates of oxygen diffusion across a red blood cell membrane from the patient. The rate indicates the blood lipid level, for example, through correlating a measured rate with a previously determined rate or range of rates for an established level of blood lipid. Advantageously, red blood cell samples are standardized to generally uniform conditions of gas content by exposing the red blood cell to oxygen and exposing the red blood cell to an environment depleted of oxygen as part of the measurement process. Preferably, the rate at which oxygen moves across the red blood cell membrane is determined by monitoring either a blood plasma level of oxygen, a level of oxygen bound to hemoglobin, or both.

In one embodiment, the method of the invention can be used to assess a patient's susceptibility to angina pectoris. This embodiment includes measuring a rate of oxygen diffusion across a membrane of a red blood cell from the patient. This rate indicates the patient's susceptibility to angina pectoris, for example, by correlating the measured rate with the susceptibility to angina observed in a control or standardized population, or in the patient, at the measured rate.

In another embodiment, the method of the invention can be used to follow the course of a lipid-lowering therapy. This embodiment includes measuring a rate of oxygen diffusion across a membrane of a red blood cell from the patient. This rate determines the effectiveness of a lipid-lowering therapy, for example, by correlating the measured rate with lipid levels to determine the patient's relative or absolute lipid level, and comparing the patient's lipid level to the patient's previous lipid levels.

The apparatus of the invention, which is suitable for conducting the methods of the invention, measures diffusion of oxygen across a red blood cell membrane and includes an oxygen level detector, a gas exchange system, and a red blood cell transport system. The red blood cell transport system is adapted and configured for transporting red blood cells through the gas exchange system and the oxygen level detector. The gas exchange system is adapted and configured to exchange gasses with the red blood cell. The oxygen level detector is adapted and configured for detecting oxygen levels in a red blood cell or in fluid (e.g., plasma) surrounding a red blood cell.

In a preferred embodiment of the apparatus, the oxygen level detector is a spectrophotometric detector, the red blood cell transport system is a pump, and the gas exchange system is a closed loop diffusion system. The preferred closed loop diffusion system includes gas permeable tubing in a chamber defined by a housing. The gas permeable tubing has a lumen effective for containing red blood cells and for diffusion of gas through the tubing and to and the red blood cells. The housing is adapted and configured for containing successive samples of gases to effect gas exchange with the red blood cells.

BRIEF DESCRIPTION OF THE DRAWINGS

FIG. 7 illustrates timecourses for oxygen release from red blood cells for patients grouped by cholesterol level.

DETAILED DESCRIPTION OF THE INVENTION

The present invention relates to a method and apparatus for measuring the rate of oxygen diffusion across a red blood cell membrane. The method and apparatus can be employed to monitor treatment of or to diagnose disorders of blood, heart, and/or circulation, such as angina pectoris, The method and apparatus can also be employed for determining a patient's blood lipid level.

Oxygen Diffusion Through Red Blood Cell Membranes
Measuring Oxygen Levels

Oxygen levels in gasses, in liquids, in blood, such as in blood cells or plasma and in tissues can be measured in several ways and using a variety of instruments that are known in the art. An oxygen electrode detects free molecular oxygen in a liquid and can be used with biological fluids such as blood, plasma, and the like. Oxygen can also be detected by known spectrophotometric methods, either free or as part of a complex with another molecule.

In red blood cells, nearly all oxygen present is complexed with hemoglobin. Such complexes can be detected by numerous methods known in the art, including spectrophotometric methods, fluorometric methods, potentiometric methods, and the like. For example, for absorption of light in the uv/visible range, the greatest difference in absorbance between hemoglobin and oxygenated hemoglobin occurs at 660 nm. At 805 nm, the isobestic point, there is no difference in absorbance between oxygenated hemoglobin and hemoglobin. Typically, scattering of light by blood components is accounted for by determining absorbance at a wavelength where neither hemoglobin nor oxygenated hemoglobin significantly absorb light. After accounting for scattering, the difference in absorbance at 660 nm yields the concentration of oxygenated hemoglobin. Various instruments exist for convenient and automated measurements of levels of oxygenated hemoglobin.

A small amount of the oxygen present in blood is not complexed with hemoglobin, and can be detected as oxygen in plasma. Plasma oxygen can be detected by numerous methods known in the art, including spectrophotometric methods, fluorometric methods, potentiometric methods, and the like. For example, excitation of a plasma sample at 385 nm results in fluorescence of plasma oxygen which is detectable at 515 nm. Light scattering can be taken into account by a measurement at a wavelength outside the range of fluorescence of absorption of oxygen in plasma. Various instruments exist for convenient and automated measurements of levels of plasma oxygen.

Figure 1:
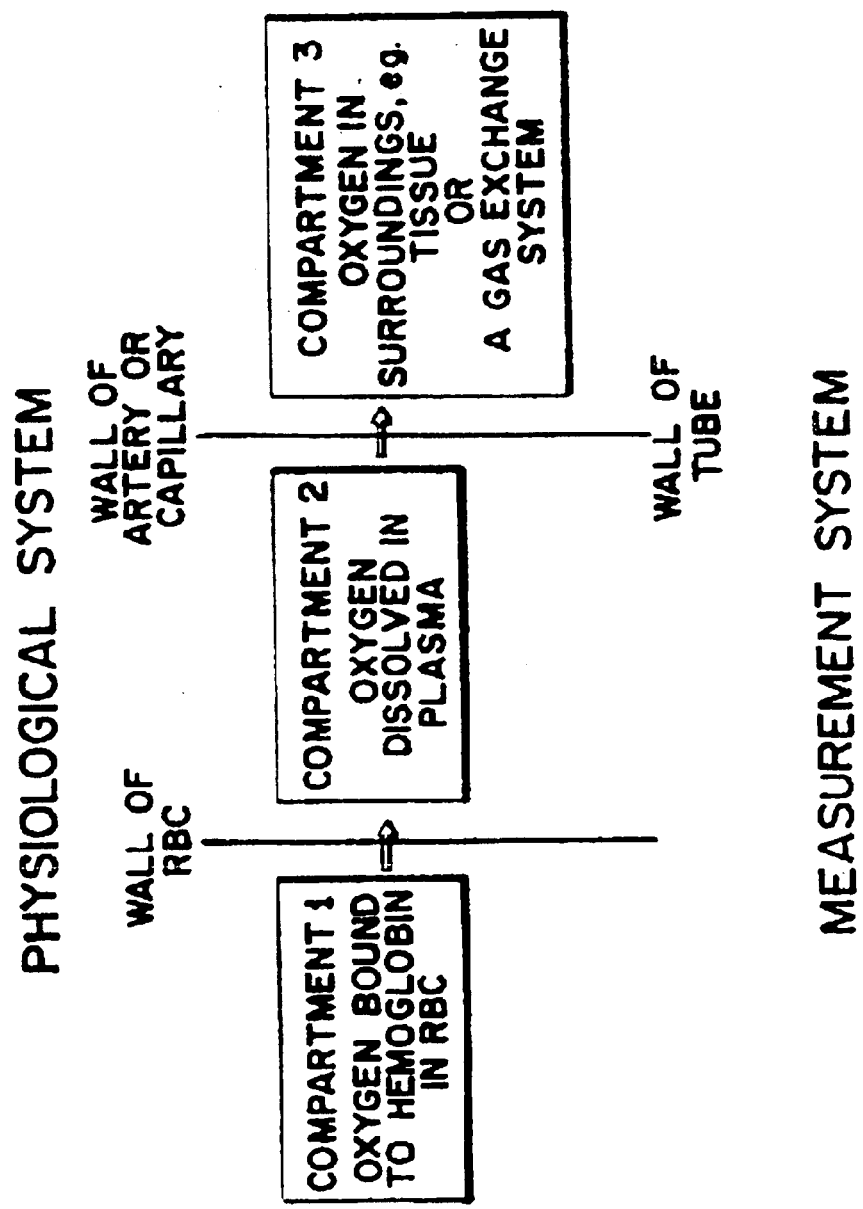
FIG. 1 illustrates three compartments associated with the circulation of blood, involved in oxygen transfer and utilization, and that can be modeled in an apparatus for measuring oxygen levels.

Employing one or more instruments that can determine oxygenated hemoglobin and determine plasma oxygen in a system allows both forms of oxygen to be determined in a single sample. Advantageously, in the method and apparatus of the invention a single instrument or detector can determine both oxygenated hemoglobin and plasma oxygen. Measurement of one or both of the plasma oxygen level and/or the level of oxygenated hemoglobin determines a rate at which oxygen crosses the red blood cell membrane to move from being oxygenated hemoglobin to being plasma oxygen. Either or both of these levels can be monitored continuously or intermittently. Alternatively, measuring an amount or level after a predetermined time period can also yield a rate of diffusion across the red blood cell membrane.
Oxygen in Blood, Tissues, and Model Systems FIG. 1 shows three compartments associated with circulation of blood, that are involved in oxygen transfer and utilization, and that can be modeled in an apparatus for measuring oxygen levels. Oxygen levels can be measured in any or all of these compartments.

Compartment one represents the interior of a red blood cell. A red blood cell lacks a nucleus, organelles, and any internal membranous structures. The cell membrane is the only membrane of a red blood cell; the red blood cell is basically a membranous sack containing hemoglobin. Oxygen in a red blood cell faces only two barriers to exiting the cell: dissociating from hemoglobin and diffusing across the red blood cell membrane. Dissociation from hemoglobin is fast compared to diffusion across the red blood cell membrane. Therefore, the rate at which oxygen leaves a red blood cell reflects the rate at which oxygen diffuses through or across the red blood cell membrane.

The level of oxygen in compartment one is the level of oxygenated hemoglobin in the red blood cell. Only negligible oxygen in a red blood cell is free of hemoglobin. In a red blood cell, total oxygen content can be measured by any of several known methods, for example, by the amount of hematocrit, or hemoglobin and the level of oxygen saturation ($S_{O_2}$) of the hemoglobin. The level of oxygen saturation is defined by the concentration of oxygenated hemoglobin [HbO] divided by the concentration of total hemoglobin [Hb] times 100%; [HbO]/[Hb]×100%. This can be measured by a variety of methods and instruments known in the art.

Compartment two represents the blood outside of the red blood cell and can include other blood cells, proteins, plasma, serum components, laboratory additives (e.g. anticoagulants), and the like. Compartment two generally contains only a small amount of the total oxygen in blood. However, any oxygen entering or leaving the blood must cross through this compartment on its way to hemoglobin, the oxygen transport vehicle. Therefore, the level of oxygen in compartment two reflects the flux of oxygen from compartment one to compartment three, and also in the reverse direction. Oxygen levels in compartments one and three will affect the oxygen level in and the rate of change of oxygen level in compartment two.

The level of oxygen in compartment two can be represented by plasma oxygen levels. This can be measured as $P_{O2}$, the partial pressure of oxygen in plasma. This measurement can be conducted by a variety of methods and instruments known in the art. Since partial pressure measurements are affected only by gas molecules free in solution, oxygen that is bound to hemoglobin is not included in instantaneous $P_{O2}$ measurements. Over time, however, the hemoglobin does affect P02 values by acting as an oxygen sink, which removes excess oxygen from the plasma when levels are high and replaces plasma oxygen when levels are low.

Compartment three represents the surroundings of a vessel or tube carrying blood. In an animal, compartment three represents tissue that surrounds a blood vessel. Lung tissue supplies oxygen to the blood via diffusion of oxygen through the blood vessel wall and across the membrane of the red blood cell, leading to the formation of oxygenated hemoglobin. Other tissues are nourished by oxygen that dissociates from hemoglobin, crosses the red blood cell membrane, leaves the blood vessel, and enters the tissue. In an apparatus that measures oxygen levels in blood or blood components, compartment three typically represents the surroundings of a tube, such as a gas permeable silicon or silastic tube, carrying blood. In such an apparatus, compartment three can be a gas or liquid (fluid) filled container from which oxygen can diffuse through the tube and into compartments two and one. In addition, in such an apparatus, oxygen can diffuse from compartments one and two into compartment three.

In the method and apparatus of the present invention, the oxygen concentration in compartment three can be controlled. This allows control of the direction and amount of flow of oxygen into and out of compartments one and two. In the method and apparatus of the invention, measuring the amount of oxygen in either or both of compartments one and two reveals the direction and rate of movement of oxygen. For example, depletion of oxygen in compartment three will deplete oxygen in the plasma, and oxygen will dissociate from oxygenated hemoglobin, diffuse through the membrane of the red blood cell and out of the cell. When the concentration of oxygen in compartment three is higher than the concentration in compartment two, the plasma will become oxygenated, and oxygen will diffuse through the membrane of the red blood cell and into the cell, and form oxygenated hemoglobin.

Mathematical Description of Oxygen Diffusion in Tissue and Apparatus

Blood to Tissue Oxygen Transport

Although not limiting to the present invention, transport of oxygen from red blood cells to surrounding tissue can be modeled as follows.

For practical calculations, the $O_2$ content of a single red blood cell is difficult to work with. A more suitable estimate of tissue bed $O_2$ availability can be derived by calculations based on a milliliter of whole blood. Under normal physiologic conditions, each gram of hemoglobin (Hb) can bind 1.34 of $O_2$ and each 100 ml of whole blood contains about 15 g of Hb, so that each 100 ml of whole blood can bind up to 20.1 ml of $O_2$ or 0.201 ml $O_2$/ml (20 volume %). Normal arterial blood at a $pO_2$ (partial pressure of $O_2$ dissolved in the blood plasma) of 95.7 mm Hg releases about 0.045 ml of $O_2$/ml blood as the $pO_2$ drops to that of mixed venous blood where the $pO_2$ is 40 mm Hg. This process of unloading takes the $O_2$ saturation of Hb from 97% to 75%. For any Hb value, the $O_2$ concentration of saturated whole blood is equal to 1.34·g Hb/ml. By determining the red blood cell $O_2$ saturation ($SO_2$) the $O_2$ concentration of unsaturated whole blood is equal to $SO_2$·1.34 HB/ml (1).

In addition to the $O_2$ contained in the red blood cells, the blood contains $O_2$ dissolved in the plasma, which obeys Henry's law, where $[O_2]=\alpha \cdot pO_2 \cdot (1-Hct)$ ($\alpha=2.04 \cdot 10^{-5}$ ml $O_2$/mm Hg, Hct=hematocrit). At maximum plasma $pO_2$ of 149 mm Hg (1 atmosphere) and a Hct of 40%, about 0.002 ml of $O_2$ can be carried by 1 ml of plasma—about 1% of the carrying capacity of the red blood cell (2). The plasma $O_2$ content is, therefore, negligible. Rather, the primary influence of the plasma $O_2$ content on tissue oxygenation is in the plasma $pO_2$ regulation of $SO_2$.

As stated, the $SO_2$ of arterial blood delivered to the tissues under ordinary conditions is about 97%. From the $O_2$ dissociation curve of Hb, this $SO_2$ corresponds to a $pO_2$ of 95.7 mm Hg. Thus, $[O_2]_{red\ blood\ cell}=0.195$ ml $O_2$/ml blood. $[O_2]_{plasma}=0.002$ ml $O_2$/ml blood, and $[O_2]_{blood}=0.197$ ml $O_2$/ml blood. The $SO_2$ of mixed venous blood leaving the tissues under ordinary conditions is about 75% corresponding to a $pO_2$ of about 40 mm Hg. Thus, $[O_2]_{red\ blood\ cell}=0.151$ ml $O_2$/ml blood, $[O_2]_{plasma}=0.001$ ml $O_2$/ml blood, and $[O_2]_{blood}=0.152$ ml $O_2$/ml blood.

Under conditions of maximum stress and increased tissue $O_2$ demand, the $SO_2$ of arterial blood does not change appreciably. However, the $SO_2$ of mixed venous blood, equal to that of the perfused tissues, does change to a remarkable degree. The $SO_2$ of mixed venous blood leaving the tissues under conditions of maximum stress can go as low as 20% (a $pO_2$ of about 15 mm Hg). Thus, under maximum stress conditions $[O_2]_{red\ blood\ cell}=0.040$ ml $O_2$ ml blood, $[O_2]_{plasma}=0.000$ ml $O_2$/ml blood, and $[O_2]_{blood}=0.140$ ml $O_2$/ml blood. It follows that the normal $O_2$ delivery of 0.045 ml $O_2$/ml blood rises under maximum stress to 0.157 ml/$O_2$/ml blood, a 3.5-fold increase in tissue $O_2$ availability.

During normal conditions, the average blood flow in the coronary arteries is 1.06 ml/sec or 63.6 ml/min. This flow rate results in an average volume of $O_2$ delivered of 1.06 ml blood/sec·0.045 ml $O_2$/ml blood=0.048 ml $O_2$sec or 2.86 ml $O_2$/min. During conditions of maximum stress and increased cardiac output, the average blood flow per sec in the coronary arteries can increase 2.39-fold, so that the average blood flow is 2.39·1.06 ml/sec=2.53 ml/sec or 151.8 ml/min. This flow rate results in an average volume of $O_2$ delivered of 2.53 ml blood/sec·0.157 $O_2$/ml blood=0.379 ml $O_2$sec or 23.83 ml $O_2$/min. The maximum stress-induced 2.39-fold increase in coronary blood flow is designated the coronary flow reserve factor, which represents 152 ml blood/min in an unimpeded coronary arterial system.

During normal conditions, the area of the heart served by the coronary artery system (the ventricles) needs 1.3 ml $O_2$/min/100 g. During conditions of maximum stress, this value increases to 8.0 ml $O_2$/min/100 g. Reciprocal blood transit times through the heart have been calculated to be 0.2 sec$^{-1}$ to 1.0 sec$^{-1}$ (median. 0.6 sec$^{-1}$). These reciprocal blood transit times correspond to cardiac transit times of 1 to 5 sec (median, 1.6 sec). Under conditions of maximum stress, cardiac transit time decreases to less than 1 sec. The minimum $O_2$ unloading time of normal red blood cell with a membrane thickness of 1 $\mu$m has been given as 0.063 sec (2), with more likely times in vitro of 0.4 to 1.0 sec (1,5.6). These values are close to the average cardiac transit time, but still lower than cardiac transit time under maximum stress.

Oxygen Transport in a Gas Exchange Apparatus

Although not limiting to the present invention, transport of oxygen from a red blood cell to surroundings in a gas exchange apparatus can be modeled as follows.

The requirements described above for delivery of blood through the coronary arteries can be met by a coronary embodiment of the device of the invention fitting parameters described below. For example, a coronary embodiment typically will have a $SO_2$ into the apparatus of 97%, corresponding to a $pO_2$ of 95.7 mm Hg; an $SO_2$ out of the apparatus of 75%, corresponding to a $pO_2$ of 40 mm Hg (normal conditions); or an $SO_2$ out of the apparatus of 20%, corresponding to a $pO_2$ of 15 mm Hg (maximum stress conditions). These parameters describe a rate of $O_2$ delivery to the tissue of 2.86 ml $O_2$/min under normal conditions and a rate of $O_2$ delivery to the tissue of 23.83 ml $O_2$/min under conditions of maximum stress. This corresponds to a total $O_2$ delivery to the tissue of about 0.24 ml $O_2$/pass under normal conditions and a total $O_2$ delivery to the tissue of about 0.40 ml $O_2$/pass under conditions of maximum stress.

Although not limiting to the present invention, a coronary embodiment of the apparatus can be envisioned as having two compartments that are separated by a membrane or tubing barrier permeable to $O_2$ but not to a liquid such as blood plasma: In this embodiment: $V_1$=volume of the sample; $V_2$=volume of the "environment"; $C_1$=oxygen concentration in the sample; $C_2$=oxygen concentration in the "environment"; $\Delta C = C_1 - C_2$; A=membrane area; P=membrane permeability to $O_2$; $\Delta x$=membrane or tubing thickness; $(pO_2)_1$=partial pressure of $O_2$ in sample; $(pO_2)_2$=partial pressure of $O_2$ in environment; $\Delta pO_2 = (pO_2)_1 - (pO_2)_2$; $J_s$=current across membrane; $N_1$=amount of $O_2$ in sample compartment; $N_2$=amount of $O_2$ in environmental compartment. $N = N_1 + N_2$=total amount of $O_2$ in system=constant. Each of these variables can be present in a coronary embodiment including two compartments separated by a barrier permeable to oxygen.

The following equations can describe such a coronary embodiment.

$$J_s = P * \Delta C = P * \alpha * \Delta pO_2$$

Equation 1 describes the relationship between current across membrane, $O_2$ pressure gradient and concentration gradient. $\alpha$=relationship between $\Delta C$ and $\Delta pO_2$=3·10$^{-5}$ ml $O_2$/(ml blood·mm Hg).

$$N_1(t) = C_1(t) * V_1 :$$
$$N_2(t) = C_2(t) * V_2 :$$
$$N = N_1 + N_2$$

Equation 2 describes the relationship between amount of $O_2$ and volumes and concentrations in each compartment.

$$dN_1(t)/dt = V_1 * dC_1(t)/dt$$
$$dN_2(t)/dt = V_2 * dC_2(t)/dt$$

Equation 3 describes the relationship between rate of change of amount of $O_2$ and volumes and concentrations in each compartment.

Combining these equations yields equation 4 (remembering that N is a constant):

$$d(\Delta C)/dt = -A * P * \left[\frac{1}{V_1} + \frac{1}{V_2}\right] * (\Delta C)$$

Equation 4 is the differential equation derived by adding the equations for continuity and diffusion. Equation 4 has a solution of the form of equation 5:

$$\Delta C(t)/\Delta C(0) = e^{-A*P*[1/V_1 + 1/V_2]*t} = e^{\frac{t}{t_0}}$$

Equation 5 represents a solution of equation 4 for concentration as a function of time.

Equation 5 can be applied specifically to a coronary embodiment of the present apparatus as follows: In applying it to oxygen transfer through the oxygen porous tubing used in the embodiment from blood or plasma to the environment, the environment has a much larger volume than the tubing and the following approximations hold, $V_2 >> V_1$ and thus $1/V_2 \sim 0$.

The permeability constant of typical gas permeable tubing is shown in equation 6:

$$\Phi = 7961 * 10^{-10} \frac{cm^3 * mm}{cm^2 * \sec * cmHg}$$

Equation 6 describes the value of the permeability constant under physiological conditions for silicone gas permeable tubing material suitable for an apparatus of the invention. Therefore, the time constant is described by equation 7:

$$\frac{1}{t_0} = \frac{A * \Phi}{\Delta x * \alpha * V_1 * 10}$$

$\Delta C$ expressed as $\Delta pO_2$

Equation 7 describes the value a of research apparatus time constant expressed in terms of $pO_2$. One apparatus suitable for a coronary embodiment can have $\Delta x$=0.2415 mm., A=92.55 cm$^2$, $V_1$=15 ml. And $\alpha$=3.0·10$^{-5}$ ml $O_2$/ml blood/mm Hg. Therefore, for such an apparatus, equation 7 yields equation 8:

$$\frac{1}{t_0} = \frac{92.55 * 7916 * 10^{-10}}{0.2415 * 3 * 10^{-6} * 15 * 10}$$

$$\frac{1}{t_0} = 6.78 * 10^{-1} \sec^{-1}$$

Equation 8 shows the value of a time constant for one apparatus suitable for a coronary embodiment as determined by substitution of suitable values in equation 7. Under typical physiological conditions, equation 7 reduces to equation 9:

$$\frac{\ln\left[\frac{40}{95.7}\right]}{-6.78 * 10^{-2}} = t = 13 \text{ sec}$$

Equation 9 illustrates the time of oxygen to leave one apparatus suitable for a coronary embodiment for normal conditions. Under conditions of maximum stress these same equations yield, for a final oxygen pressure of 20 mm Hg, t=23.1 sec.

Due to several approximations made in this derivation, and known variations in certain of the factors included in these equations, it is believed that the interface between plasma and the gas permeable surface of an apparatus of the invention can introduce a t of from 2 to 26 seconds under typical conditions.

The above equations can be readily visualized as applying to blood, that is red blood cells and plasma, in an apparatus of the invention by envisioning that equation 5 applies to the diffusion from the red blood cell, with compartment one referring to the red blood cell and 2 referring to the plasma. The volume of the plasma is assumed to be much greater than that of the red blood cell, thus $1/V_2 \approx 0$, as in the above derivation. Further, the $O_2$ content of the plasma can be assumed to be nearly 0 since $\alpha$ is so small. Since the method and apparatus of the invention can employ oxygen saturation. $SO_2$, for a measurement of C in a red blood cell, the method and apparatus can relate this to the concentration. Equation 9 leads to equation 10, which shows this relationship. Equation 10:

$$d(\Delta C)/dt = -A * D_o * \left[\frac{1}{V_t}\right] * (\Delta C)$$

Equation 10 is a preliminary step on the way to equation 12 showing Differential equation derived by adding the equations for continuity and diffusion for red blood cells. In equation 10, $D_o$ is the oxygen diffusion coefficient for the red blood cell. The concentration of oxygen relates to the $SO_2$ by equation 11:

$$[O_2] = SO_2 * 1.34 \frac{mlO_2}{gHb} * \frac{gHb}{mlblood} \approx SO_2 * 20.1 \frac{mlO_2}{mlblood}$$

Equation 11 describes the relationship between oxygen concentration and oxygen saturation in the red blood cell. This leads to a solution of equation 11 in terms of $SO_2$ shown in equation 12.

$$SO_2(t) = SO_2(0) * e^{\frac{t}{t_0}} : \frac{1}{t_0} = \frac{A * D_o}{V_1 * 20.1}$$

Equation 12 shows a solution of equation 8 in terms of oxygen saturation in a red blood cell. The value of $D_o$ as $9.5 \cdot 10_{-6}$ cm$^3$/sec is known to be and the value of $V_1/A$ is approximately $1 \cdot 10^{-4}$ cm. Thus, equation 13 is:

$$\frac{1}{t_0} = \frac{9.5 * 10^{-6}}{1 * 10^{-6} * 20.1} = 4.73 * 10^{-3} \text{ sec}^{-1}$$

Equation 13 describes the value for the time constant of the diffusion of oxygen from the red blood cell using a large, it is believe the largest reasonable value of $D_o$. A smaller, but still reasonable, value of $D_o$ including the "dead space" around the red blood cell is 2.0 to $4.0 \cdot 10^{-7}$ cm$^3$/sec. This increases the time constant of the red blood cell as shown in equation 14.

$$\frac{1}{t_0} = \frac{4.0 * 10^{-7}}{1 * 10^{-4} * 20.1} = 2 * 10^{-4} \text{ sec}^{-1}$$

Equation 14 describes the value for the time constant of the diffusion of oxygen from the red blood cell using a smaller, but still reasonable value of $D_o$.

Applying these values for the red blood cell to a normal case ($SO_2(t)=75\%$) and a maximum stress case ($SO_2(t)= 20\%$), both with initial values of 97%, the times for discharge are in equations 15 and 16 for the higher value of the diffusion constant and equations 17 and 18 for the lower value of the diffusion constant.

$$\ln\left[\frac{.75}{.97}\right] = -4.73 * 10^{-1} * t : t = 54.3 \text{ seconds}$$

Equation 15 describes the time for red blood cell oxygen diffusion under normal conditions with higher $D_o$.

$$\ln\left[\frac{.75}{.97}\right] = -2 * 10^{-4} * t : t = 1286 \text{ seconds}$$

Equation 16 describes the time for red blood cell oxygen diffusion under normal conditions with lower $D_o$.

$$\ln\left[\frac{.20}{.97}\right] = -4.73 * 10^{-1} * t : t = 333.8 \text{ seconds}$$

Equation 17 describes the time for red blood cell oxygen diffusion under maximum stress with higher $D_o$.

$$\ln\left[\frac{.20}{.97}\right] = -2 * 10^{-1} * t : t = 7895 \text{ seconds}$$

Equation 18 describes the time for red blood cell oxygen diffusion under maximum stress with lower $D_o$.

These equations illustrate that the time required for oxygen to diffuse from a red blood cell to the plasma are long compared with the times required for oxygen to diffuse through a tubing or membrane employed in the present invention. Therefore diffusion through such tubing or membrane is fast and does not hinder measurement of rates of diffusion of oxygen through the cholesterol containing membrane of the red blood cell.

Measuring Oxygen Diffusion Across a Red Blood Cell Membrane

The lipid content, particularly the cholesterol content, of the red blood cell membrane is believed to be a factor that affects the diffusion of oxygen through the red blood cell membrane. The cholesterol content of the red blood cell membrane in turn reflects blood cholesterol levels. Therefore, the rate at which oxygen crosses the red blood cell membrane provides a measure of blood cholesterol levels and is useful in diagnosis and treatment of coronary artery disease and other heart and circulatory disorders. The present invention includes a method for measuring the rate at which oxygen diffuses across the red blood cell membrane, which includes embodiments directed to methods of evaluating lipid-lowering treatments, methods of diagnosing or assessing the risk of heart and circulatory disorders such as angina pectoris, and methods of determining a patient's blood lipid level.

The present method of determining a patient's blood lipid level typically includes the steps of obtaining a blood sample from a patient, measuring a rate of oxygen diffusion across a membrane of a red blood cell, and, preferably, correlating the measured rate with established levels of blood lipid to determine the patient's blood lipid level.

The step of measuring the rate of oxygen diffusion across a membrane of a red blood cell preferably includes the steps of exposing the red blood cell to oxygen; exposing the red blood cell to an environment depleted of oxygen; and monitoring either a blood or plasma level of oxygen, a level of oxygen bound to hemoglobin, or both. A blood sample obtained from a patient or subject can contain varying amounts of oxygen, and the rate at which oxygen crosses the red blood cell membrane can, in certain conditions, depend on the amount of oxygen present. Exchanging gasses, either by exposing the red blood cells to oxygen or by exposing the red blood cell to an environment depleted of oxygen, standardizes the blood sample to a predetermined level of oxygen and allows significant comparison of numerous blood samples. The red blood cell can be first exposed to oxygen and subsequently exposed to an environment depleted of oxygen. When exposure to oxygen precedes depletion, oxygen is released from red blood cells during and after depletion, and monitoring, typically, monitors this release. Alternatively, the red blood cell can be first exposed to an environment depleted of oxygen and subsequently exposed to oxygen. When depletion of oxygen precedes exposure to oxygen, oxygen is taken up by the red blood cells during exposure, and monitoring, typically, monitors this uptake.

In a preferred embodiment, exposing the red blood cell to oxygen includes circulating a blood sample in a closed loop diffusion system 17 Typically the closed loop diffusion system 17 includes a chamber 13 containing an atmosphere including oxygen. The level of oxygen in chamber 13 can be varied and be controlled over a wide range. The red blood cells can be exposed to any concentration suitable for standardizing the oxygen level between no oxygen and 100% oxygen. Preferably, the partial pressure of oxygen in chamber 13 is approximately oxygen's partial pressure in air. That is, the atmosphere in chamber 13 includes oxygen at atmospheric gas pressure, for example, 160 mm Hg $O_2$ with 4 mm Hg $CO_2$. Alternatively, the partial pressure of oxygen in chamber 13 can be approximately oxygen's partial pressure in a capillary. That is, the atmosphere in chamber 13 includes oxygen at a pressure, for example, of about 23 mm Hg $O_2$ with 46 mm Hg $CO_2$. Preferably the blood reaches equilibrium with oxygen or with both oxygen and carbon dioxide. In one embodiment, this step of circulating the blood in the closed loop system lasts for about 0.1 to about 60 minutes.

In a preferred embodiment, exposing the red blood cell to an environment depleted of oxygen includes circulating a blood sample in closed loop diffusion system 17 with closed loop diffusion system 17 including chamber 13 containing an atmosphere depleted of oxygen. For example, a suitable oxygen depleted atmosphere is nitrogen or another inert gas, preferably nitrogen. Typically, a commercial or medical grade of nitrogen gas can be employed. Preferably, this depleting step results in complete or nearly complete removal of oxygen from chamber 13, gas permeable tubing 15, and the fluid containing the red blood cells (e.g., plasma). Although considerable deoxygenation is typically observed in the first about 30 seconds, typically, this circulating step lasts longer, preferably, in one embodiment about 15 minutes.

Monitoring either a blood level of oxygen, a level of oxygen bound to hemoglobin, or both can be accomplished employing a variety of methods or instruments, as described herein. Monitoring can take place continuously or intermittently through the exposing and circulating steps, or only at two or more discrete time points. For example, the method can include the step of determining the level of saturation of hemoglobin with oxygen achieved during the step of exposing the red blood cell to oxygen.

In one embodiment, measuring the rate of oxygen diffusion across a red blood cell membrane includes monitoring the ratio of $S_{O2}/P_{O2}$ and plotting this ratio as a function of time under the following conditions:
 a) The blood sample is oxygenated, preferably to its maximum, by subjecting compartment three to 1–100% oxygen. Then, $S_{O2}/P_{O2}$, $S_{O2}$, and/or $P_{O2}$ can be measured.
 b) The blood sample is subjected to a 0% oxygen environment (e.g., 100% nitrogen or another inert gas) in compartment three. Then, $S_{O2}/P_{O2}$, $S_{O2}$, and/or $P_{O2}$ can be measured, preferably continually, over time.

In these conditions, free oxygen has been depleted, but oxygenated hemoglobin remains a source of oxygen. Release of oxygen from oxygenated hemoglobin, which decreases the level of oxygenated hemoglobin, supplies oxygen to the plasma by diffusion through the red blood cell membrane. To the extent that this diffusion is slowed by the membrane, the plasma levels of oxygen ($P_{O2}$) remain depressed and the oxygen saturation ($S_{O2}$) of the hemoglobin remains high for a longer period. Therefore, the rate at which plasma oxygen levels increase, and the rate at which oxygen saturating levels decrease, provide a measure of the rate of diffusion of oxygen through the red blood cell membrane.

Figure 2:
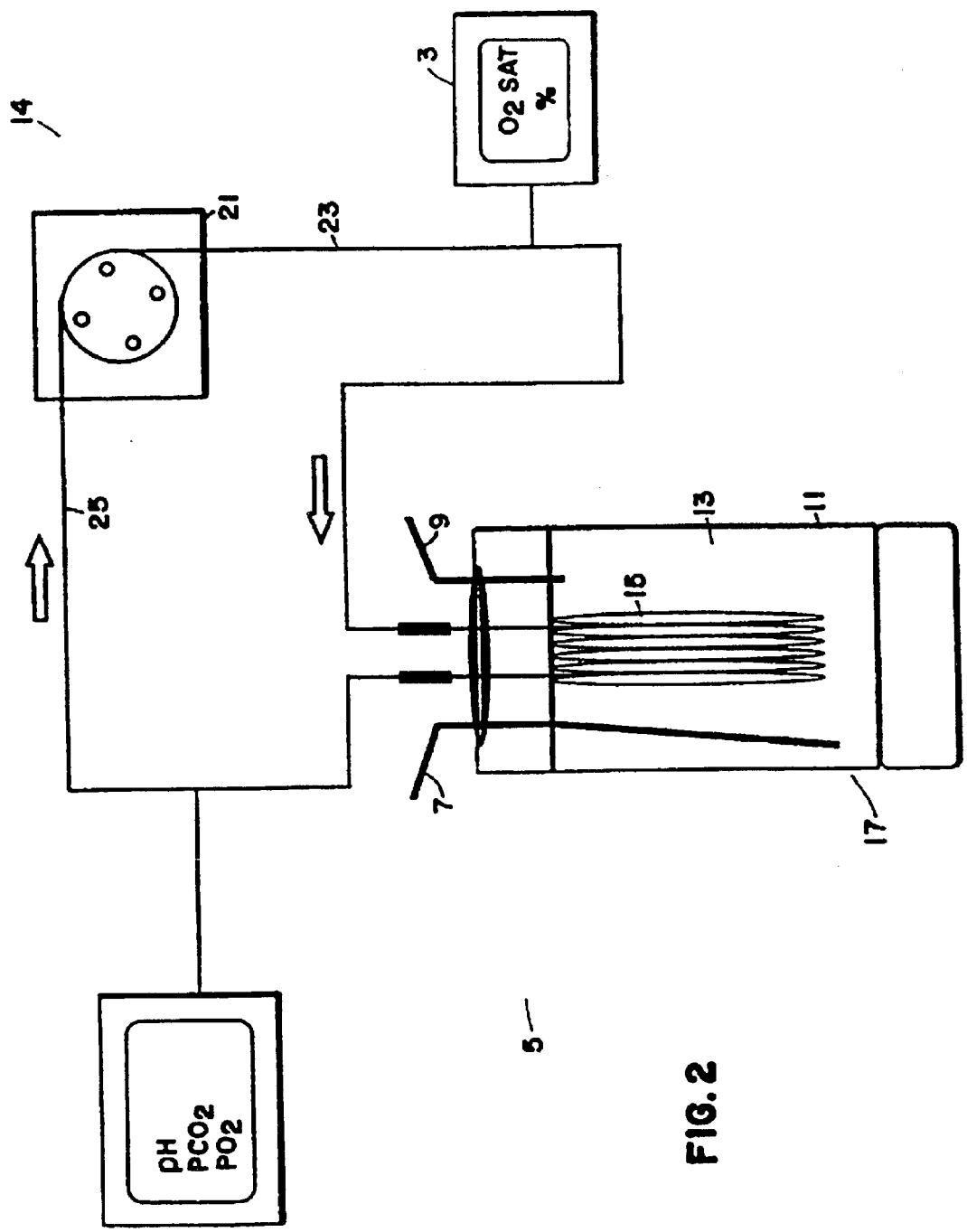
FIG. 2 illustrates an embodiment of the apparatus of the invention.

Apparatus for Measuring the Rate of Oxygen Diffusion Across a Red Blood Cell Membrane FIG. 2 illustrates an apparatus for measuring the rate of oxygen diffusion across a red blood cell membrane. The apparatus includes an oxygen level detector, a gas exchange system, and a red blood cell transport system. The red blood cell transport system is adapted and configured for transporting red blood cells through the gas exchange system and the oxygen level detector. The gas exchange system is adapted and configured to exchange gasses with the red blood cell. The oxygen level detector is adapted and configured for detecting oxygen levels in a red blood cell or in fluid surrounding a red blood cell.

Oxygen level detector 3 can be any of several detectors suitable for detecting oxygen levels in plasma or another fluid and/or for detecting oxygenated hemoglobin or another oxygen complex. For example, oxygen detector 3 can include an oxygen electrode, a spectrophotometric detector, a fluorometric detector, or a combination of such electrodes and/or detectors. Preferably, oxygen level detector 3 includes detectors for spectrophotometric determination of both plasma oxygen and oxygenated hemoglobin. In another preferred embodiment, oxygen level detector 3 includes detectors for determination of oxygenated hemoglobin. Preferably in one embodiment, oxygen level detector 3 is a dual or multiple wavelength spectrophotometer. Oxygen level detector 3 can be any of a variety of known or commercially available oxygen level detectors.

Preferably, oxygen level detector 3 includes: a light source capable of producing light of 385 nm, 660 nm, 805 nm and an absorption free wavelength; one or more filters to sequentially submit a blood sample to these wavelengths; a cell to allow blood to flow slowly through this light system; and photopickups to detect the transmission of light through the sample at each wavelength. Preferably, oxygen level detector 3 is coupled to appropriate electronics and microprocessors to derive the amounts of, or changes in amounts of, plasma oxygen and/or oxygenated hemoglobin from the comparative signals.

Gas exchange system 5 typically includes a source of gas (not shown), a gas inlet 7, a gas outlet 9, a housing 11 that defines a chamber 13, and a gas permeable tubing 15. These components are typically assembled as a closed loop diffusion system 17, Gas permeable tubing 15 has a lumen (not shown) that is used to contain, preferably flowing, fluid containing red blood cells. A preferred fluid containing red blood cells is blood that has been treated with an anticoagulant. Gas permeable tubing 15 is constructed to allow diffusion of gasses from chamber 13 into the lumen and into any fluid in the lumen and is preferably made of silicone or silastic material. Gas permeable tubing 15 may be a cartridge-type insert which can be easily removed and discarded, after which a new, sterile gas permeable tubing 15 cartridge can be inserted. A removable, and preferably disposable, tubing cartridge increases the testing productivity of the apparatus by drastically decreasing the amount of time lost to cleansing and sterilizing the gas permeable tubing 15 between tests. Further, disposable tubing cartridges decrease the possibility of cross contamination of blood samples, which may lead to inaccurate readings.

Gas is introduced into chamber 13 through gas inlet 7, and exits through gas outlet 9. Preferably, gas flows through chamber 13 to remove any gas that diffuses from gas permeable tubing 15 and to replace any gas the diffuses into gas permeable tubing 15. Housing 11 can be a stoppered laboratory flask, such as an Erlenmeyer flask. Gas exchange system 5 can be any of several suitable systems for exchanging gas into red blood cells, blood, or another fluid.

Red blood cell transport system 19 typically includes a pump 21, inflow tubing 23 and outflow tubing 25. Red blood cell transport system 19 transports plasma or another fluid containing red blood cells through one or more oxygen level detectors 3, into gas exchange system 5, and from gas exchange system 5 back to pump 21. Preferably, pump 21 is a peristaltic pump. Alternatively, red blood cell transport system 19 can include an aspirator, an apparatus that causes flow based on capillary action, or any of several other suitable apparatus for transporting fluids containing red blood cells. Typically, red blood cell/transport system 19 includes components necessary for monitoring and recording flow rates and like characteristics as a function of time.

According to the method of the present invention, the apparatus can measure either the plasma oxygen level ($P_{O2}$) or the oxygen saturation ($S_{O2}$) of the hemoglobin, or both.

The time for measuring the oxygen saturation level is typically faster than the measurement time of the plasma oxygen level. Additionally, the rate of change of the oxygen saturation level is faster than the rate of change of the plasma oxygen level, thus an accurate $S_{O2}$ level can be determined in a shorter time period.

The cycle time to perform a test, that is, to determine the oxygen diffusion rate across the red blood cell membrane can be regulated by the components of the apparatus. In particular, the gas permeable tubing 15 can be sized to provide the desired test cycle time. For example, a smaller diameter tubing provides more surface area per volume of blood sample, thereby decreasing the time for diffusion from the blood sample. A decrease in the thickness of the tubing can also decrease the diffusion time. Various shapes of tubing can also decrease the time by increasing the surface area; tubing cross sections such as flat or rectangular shapes provide more surface area per volume than does a circular cross section. A longer tubing length will also increase the surface area. However, the sample size might have to be increased, which can be disadvantageous because a smaller blood sample volume will provide quicker results.

Once the $S_{O2}$ or $P_{O2}$ rate is determined, the apparatus records and/or displays the value. The apparatus may be configured to provide a final rate, a rate at a determined time period, or an average rate. For some tests it may be desirable for the apparatus to provide a continuous rate display or a graphical representation of the rate over time.

Figure 3:
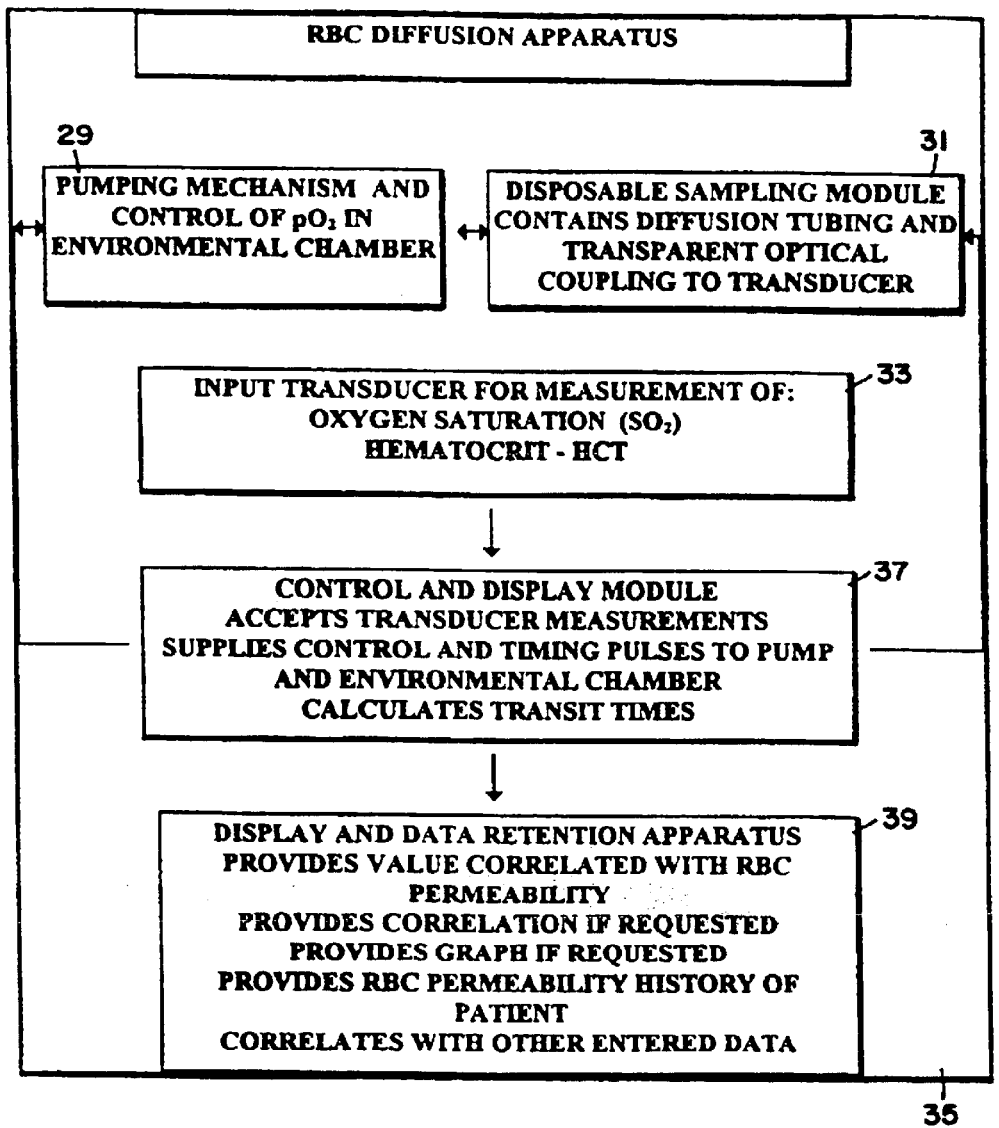
FIG. 3 is a schematic illustration of a preferred embodiment of an apparatus according to the invention.

FIG. 3 is a schematic illustration of a preferred embodiment of an apparatus according to the invention. This preferred embodiment is illustrated around five components. The gas exchange system 3, includes a chamber 13, which in this embodiment is the first component, an environmental chamber 27. Red blood cell transport system 19 includes the second and third components, a pump system 29 and a sample receiving and diffusion system 31, respectively. The fourth component, a measuring system 33, includes oxygen level detector 3. The fifth component is a control system 35. Each component is coupled, for example, either mechanically or electrically, to one or more of the other components. Each of the components operates cooperatively with one or more of the other components. Such coupling and cooperation is described below. Each of these components in a preferred embodiment can have a variety of preferred characteristics.

For example, a preferred environmental chamber 27 can cycle under one or more of the following sets of conditions. First, at the start of the measurement the chamber houses an oxygen atmosphere at a concentration and in a configuration capable of increasing the $SO_2$ of an about ten ml blood sample in the sample receiving and diffusion system 31 to above about 97.5% in no more than about 1 minute. Second, for a measurement under normal conditions, the chamber houses an atmosphere of $pO_2$ (about 40 mm Hg) in a configuration capable of decreasing $SO_2$ of an about ten ml blood sample in the sample receiving and diffusion system 31 to about 75% or less in a short time. Third, for a measurement under maximum stress conditions, the chamber houses an atmosphere of pO2 (about 20 mm Hg) in a configuration capable of decreasing $SO_2$ of a ten ml blood sample in the sample receiving and diffusion system 31 to about 40% or less in a short time. In this context a short time is less than about 20 min, preferably less than about 6 min, preferably less than about 2 min.

A preferred pump system 29 can maintain a steady or rapid pulsatile flow of 10 ml of blood without touching the sample (e.g., through tubing). A preferred pump system 29 includes a control system 35 that can interface with automated (e.g. PC based) laboratory data acquisition and control systems, such as a PC Labview system, or other automated systems as required to control, calibrate, or validate pump system 29. Pump system 29 can pump blood or another fluid containing red blood cells through the sample receiving and diffusion system 31 at a rate sufficient for environmental chamber 27 to effect the diffusion conditions described above.

A preferred sample receiving and diffusion system 31 can receive a sample from an operator of the apparatus and, with power provided by the pump, cycle the sample through environmental chamber 27. A preferred sample receiving and diffusion system 31 can receive an approximately 10 ml or smaller sample of whole blood from a syringe or vacutainer. Preferably, the blood sample has a volume less than about 3 ml, preferably less than about 1 ml. The pump and receiving and diffusion system 31 work to cycle the blood sample through environmental chamber 27 at a rate sufficient for diffusion as described above. Further, a preferred receiving and diffusion system 31 can be flushed of blood and filled with air or liquid, typically in a short time such as less than one minute.

A preferred receiving and diffusion system 31 is adapted and configured to cooperate with environmental chamber 27 to achieve the oxygen diffusion conditions described above. The time for equilibration under a given sequence of conditions of oxygen diffusion is short enough to provide a convenient test in a medical laboratory. For example, a simple comparative test can be conducted in less than about 20 min, preferably less than about 6 min, more preferably less than about 2 min. A more complex time course test can be conducted and analyzed in less than about 40 min, preferably less than about 15 min, preferably less than about 5 min.

A preferred receiving and diffusion system 31 is adapted and configured as a modular system that reversibly couples to the remainder of the apparatus of the invention. Advantageously, the modular system is constructed and priced to be disposable. For example, such a modular system can reversibly snap or clip into the remainder of the apparatus, fitting similarly to a audio or video cassette into a player. That is, such a modular system can couple both to pump system 29 for pumping fluid through receiving and diffusion system 31, and to measuring system 33 for measuring characteristics (such as oxygen content) of the blood in receiving and diffusion system 31.

For safety in handling blood, a preferred receiving and diffusion system 31 is adapted and configured so that when filling, coupling to the apparatus, or uncoupling from the apparatus, no blood leaves the system. In this way, an operator cannot come into contact with blood from the system.

A preferred measuring system 33 can monitor either $pO_2$ and/or $SO_2$, preferably noninvasively. Advantageously, a measuring system 33 can monitor the $pO_2$ of the gas mixture over a range sufficient to provide the diffusion conditions described above. For example, the range of $pO_2$ is advantageously from about 100 mm Hg to about 20 mm Hg. Advantageously, a measuring system 33 can monitor the $SO_2$ of a blood, or other, sample over a range sufficient to provide the diffusion conditions described above. For example, the range of $SO_2$ is advantageously from about 100% to about 40%, or less. Advantageously, each measurement is made with accuracy and reproducibility sufficient to detect alterations in cholesterol levels produced by therapy such as diet or medicine or to detect alterations in the ability of red blood cells to deliver oxygen to the heart.

Measuring system 33 can measure $SO_2$ or $pO_2$ with a frequency suitable for making simple two point comparisons of values, or for measuring a timecourse of oxygen release or uptake. Measuring system 33 can take a measurement in response to the operator, according to a predetermined program for measurement, by a combination of such procedures, and the like. Advantageously, a measuring system 33 can measure $SO_2$ at least once each 15 seconds in a predetermined program. Preferably, measuring system 33 is adapted and configured for providing a signal communicating the measurement and any associated information to a processor or computer for control and data gathering.

Measuring system 33 can advantageously be calibrated to assure accuracy and precision of measurements of oxygen amounts. For example, a standard solution can be place in position for measurement. The standard solution can be in a specialized calibration module, such as a receiving and diffusion system 31 adapted to contain a standard solution and, advantageously, to communicate to the apparatus that a calibration standard is in the apparatus. Alternatively, a one or more standard solutions can be sequentially added to a typical receiving and diffusion system 31 and the system can be calibrated according to the solution in the system.

The apparatus can be controlled by employing a control system 35 that, for example, controls calibration, display, mechanical actions (e.g., pumping), and measurement by the apparatus. Control system 35 can be manipulated by the operator and/or by a predetermined program to, for example, calibrate the apparatus, monitor that the apparatus is within calibration, start and stop pump system 29 and any other mechanical or electrical systems of the apparatus, recognize a properly inserted receiving and diffusion system 31, and control and communicate with the measurement system.

Control system 35 can incorporate a processor 37 for displaying and performing analysis of measurements taken by the apparatus. For example, advantageously control system 35 can gather $SO_2$ measurement data at least about each 15 seconds and then plot natural log $SO_2$ against time. From such data, a preferred control system 35 can calculate the slope of the plot permeability of red blood cells. Advantageously control system 35 includes data retention apparatus 39 that provides for statistical analysis of any measurements and data entry of additional patient or clinical information either by the operator or another processor, and the like. Such information can include a hematocrit, cholesterol level, and the like. A preferred control system 35 can display the information and test or measurement data either as a table or graph, and provide output suitable for screen display or printing. Control system 35 can include a screen and/or printer suitable for display and/or printing.

Advantageously control system 35, preferably employing data retention apparatus 39, can store, by methods standard in the data processing arts, patient data either to internal memory or to remote memory, patient data and then correlate patient data from a test with patient data from other, typically previous, tests on the same patient. Alternatively, control system 35 can access a database of population data for patient populations similar to or contrasting with the current patient, and conduct comparison of the current patient data with the population data.

Oxygen Diffusion, Cholesterol Levels, and Angina

The rate (or amount in a unit of time) of oxygen diffusion through a red blood cell membrane has been shown to correlate with blood lipid, particularly cholesterol, levels in the cell membrane and in plasma. This knowledge makes the rate of oxygen diffusion though red blood cell membranes useful in treatment and diagnostic regimes for numerous heart or circulatory disorders. Since the present method and apparatus require only a blood sample, they offer an alternative to existing methods, such as arteriography, and are noninvasive and less expensive. In addition, the present device and method allow earlier monitoring of therapy rather than waiting for a noticeable effect on a parameter such as the diameter of a coronary artery.

Treatment of most heart and circulatory disorders involves therapy, such as administration of medicines, directed at lowering a patient's blood lipid levels. Current methods of following the cardiovascular progress of lipid-lowering therapies are expensive and time-consuming. In one embodiment, the method of the invention can be used to follow the course of such lipid-lowering therapy. This embodiment includes measuring a rate of oxygen diffusion across a membrane of a red blood cell of the patient. This rate determines the effectiveness of a lipid-lowering therapy, for example, by correlating the measured rate with lipid levels to determine the patient's relative or absolute lipid level, and comparing the patient's lipid level to the patient's previous lipid levels.

Certain heart and circulatory disorders, such as angina pectoris, have a frequency and severity that correlate with blood levels of cholesterol and like lipids. In one embodiment, the method of the invention can be used to assess a patient's susceptibility to angina pectoris. This embodiment includes measuring a rate of oxygen diffusion across a membrane of a red blood cell from the patient. This rate indicates the patient's susceptibility to angina pectoris, for example, by correlating the measured rate with the susceptibility to angina observed in a control population, or in the patient, at the measured rate.

Angina can also be related to insufficient delivery of oxygen to the tissue of the heart. Under high stress blood is in the arteries supplying the heart for a shorter time than during periods of low stress. Therefore, the rate at which oxygen diffuses out of the red blood cell and the blood vessel may be too slow to release oxygen during the short residence time in the heart during high stress. This rate may be sufficient to deliver oxygen to the tissue during the longer residence times of low stress. Thus, the present method can provide another way to assess susceptibility to angina based on the correlation with residence time of blood in the heart. This method also includes measuring a rate of oxygen diffusion across a membrane of a red blood cell from the patient. This rate indicates the patient's susceptibility to angina pectoris, for example, by correlating the measured rate with the susceptibility to angina observed in a control population, or in the patient, at the measured rate, and, optionally, correlating the measured rate with residence time of blood in the heart during stress.

The present invention may be better understood with reference to the following examples. These examples are intended to be representative of specific embodiments of the invention, and are not intended as limiting the scope of the invention.

EXAMPLES

Example 1

Correlation of Cholesterol Levels with Red Blood Cell Oxygen Diffusion in an Animal Model This study determined a correlation between the level of a blood lipid, cholesterol, and the rate at which oxygen diffused out of red blood cells.

Materials and Methods

Ten New Zealand White Rabbits were divided into an experimental group and a control group. The six experimental rabbits were fed for eight weeks a diet of standard laboratory rabbit chow supplemented with 0.25% cholesterol. The four control rabbits received, for the same period, the same diet lacking the added cholesterol. After eight weeks on this diet, blood samples were collected from each rabbit by standard methods using sodium heparin as an anticoagulant. The plasma and red blood cell cholesterol levels were determined in an aliquot of each blood sample by the Allain's assay and Abell's methods, each of which is a standard method.

Figure 4:
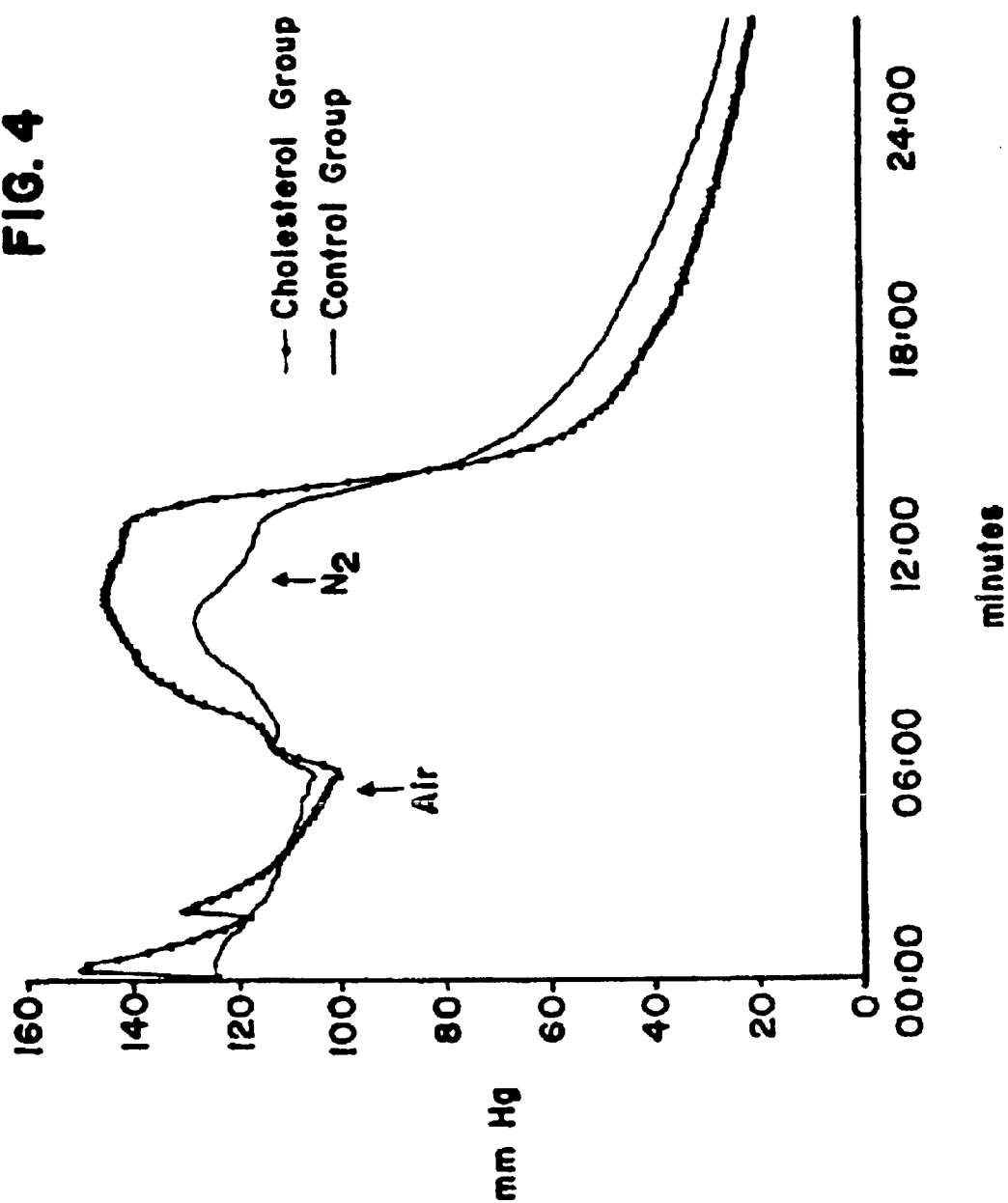
FIG. 4 illustrates the plasma oxygen levels for cholesterol-fed and control animals as determined by an embodiment of the method of the invention.

Another aliquot of each blood sample was circulated through a closed loop diffusion chamber in gas permeable tubing and exposed to atmospheric pressures of oxygen (160 mm Hg) and carbon dioxide (4 mm Hg) for 6 minutes (time 6–12 minutes in FIG. 4). This was considered full saturation of the blood with oxygen. Each blood sample was then subjected to desaturation by circulating the blood sample through the closed loop diffusion chamber and exposing the sample to nitrogen gas for 15 minutes (time 12–27 minutes in FIG. 4). During exposure to oxygen and during exposure to nitrogen, each sample was subjected to continuous blood gas monitoring for pH, $P_{CO_2}$, and $P_{O_2}$.

Results

The results of this study are shown in Table 1 and FIG. 4. Table 1 illustrates that the experimental cholesterol-fed animals had higher levels of cholesterol both in their plasma and in their red blood cell membranes than the control animals.

This higher level of cholesterol in plasma and in red blood cell membranes correlated with slower diffusion of oxygen through the red blood cell membrane (FIG. 4). FIG. 4 shows that the cholesterol-fed animals achieved higher levels of plasma oxygen during the saturation phase due to slower uptake by the red blood cells. When the cells were exposed to the nitrogen atmosphere, oxygen was exchanged out of the cholesterol-fed rabbit plasma more quickly than the control rabbit plasma. This indicates that red blood cell oxygen diffused more slowly into the plasma from the red blood cells from the cholesterol-fed rabbits than in the control blood.

TABLE 1

Cholesterol levels in rabbit plasma and red blood cell membranes in control and experimental groups after eight weeks of feeding.

| | Cholesterol (mg/dl) | | | |
|---|---|---|---|---|
| | Plasma | | Red Blood Cell Membrane | |
| Group | Mean | SEM | Mean | SEM |
| Control | 60 | ± 1.2 | 22 | ± 1.7 |
| Cholesterol | 928 | ± 31* | 121 | ± 3* |

*$p < 0.05$ vs. Control Group

Conclusion

Oxygen diffused more slowly across the red blood cell membranes of animals with the higher level of cholesterol in plasma or in red blood cell membrane. This indicates that the rate of diffusion of oxygen across a red blood cell membrane correlates with increased levels of the blood lipid cholesterol in an animal model commonly used in this field for study of blood lipids.

Example 2

Correlation of Cholesterol Levels With Red Blood Cell Oxygen Diffusion in Humans Study 1

This study determined a correlation between the level of a blood lipid, cholesterol, and the amount of oxygen that diffused into human red blood cells in 15 minutes.

Materials and Methods

Blood samples were collected by standard methods from four informed human volunteers with varying cholesterol levels. Cholesterol levels were determined in one aliquol of each blood sample by Abell's assay, a standard method. Another four aliquots from each blood sample were subjected to blood gas analysis as follows: Each aliquot was subjected to desaturation as described in Example 1 and the amount of oxygen bound to hemoglobin (Hb) was determined. Then, the aliquot was circulated through a diffusion chamber and exposed to capillary gas pressures, 23 mm Hg of $O_2$ and 46 mm Hg $CO_2$. After 15 minutes of circulation, the amount of oxygen bound to hemoglobin (Hb) was determined again.

Results

The results of this study are presented in Table 2. The results presented in Table 2 show that the amount of oxygen that crossed the red blood cell membrane decreased as the cholesterol level increased.

TABLE 2

Correlation with cholesterol levels of amounts of oxygen bound to hemoglobin in human red blood cells before and after exposure to oxygen.

| | | $O_2$ Content (ml/gm of Hb) | | | | | |
|---|---|---|---|---|---|---|---|
| | P Chol | Pre-Diffusion | | Post-Diffusion | | % | p |
| Sample | (mg/dl) | Mean | SEM | Mean | SEM | Change | Value |
| A | 87 | 13.3 ± | 0.391 | 20.5 ± | 0.478 | 35% | 0.037 |
| B | 157 | 14.8 ± | 0.091 | 19.5 ± | 0.270 | 24% | 0.041 |
| C | 241 | 15.8 ± | 0.013 | 20.2 ± | 0.551 | 22% | 0.020 |
| D | 400 | 16.3 ± | 0.079 | 17.5 ± | 0.196 | 7% | 0.014 |

Conclusion

Oxygen diffused more quickly across the red blood cell membranes of humans with the lower level of cholesterol. This indicates that the rate of diffusion of oxygen across a red blood cell membrane correlates inversely with increasing levels of the blood lipid cholesterol in humans.

Study 2

This study determined that plasma cholesterol levels and red blood cell membrane cholesterol levels in humans inversely correlate with the rate of oxygen diffusion from the human subject's red blood cell.

Materials and Methods

In this second study, venous blood was collected from 22 volunteers, standardized to a hematocrit level of the blood of 40%, and circulated in a closed-loop $O_2$ diffusion chamber to full saturation and subjected it to desaturation, while continuously measuring the $O_2$ saturation.

Figure 5A:
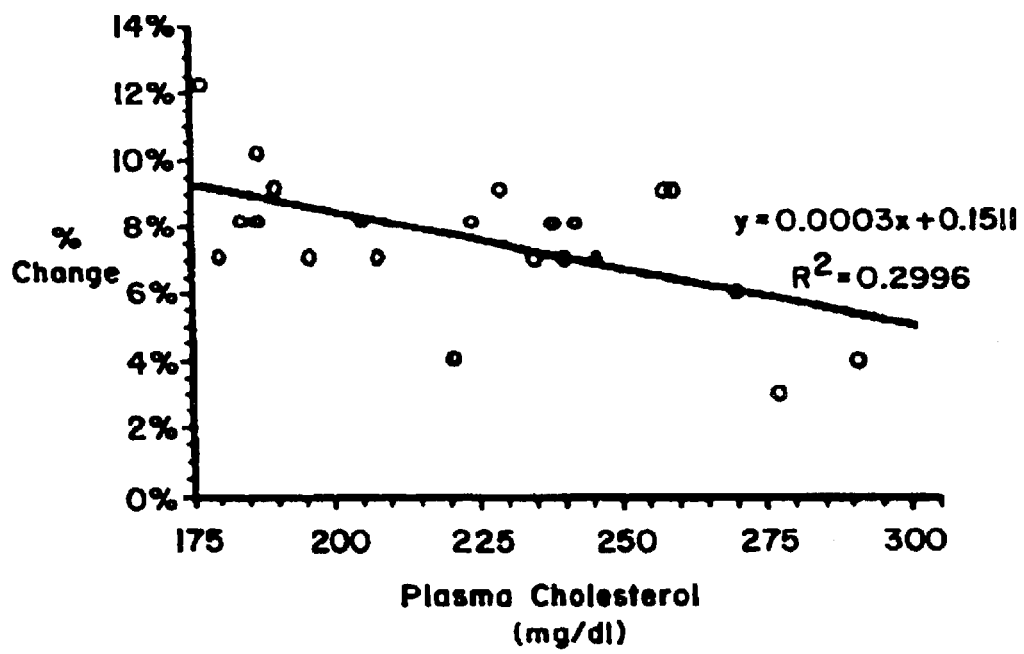
FIGS. 5a and 5b illustrate the correlation of plasma cholesterol and red blood cell membrane cholesterol levels with percent changes per unit time in $O_2$ saturation.
Figure 5B:
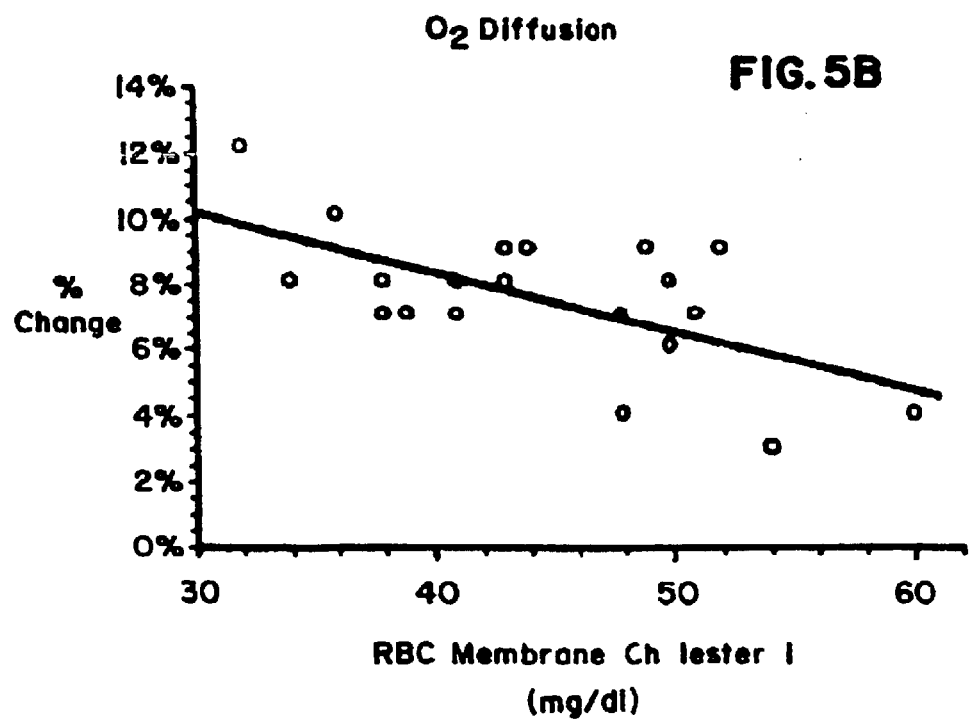

Results $O_2$ diffusion from inside to outside the red blood cell was represented by the percent change of $O_2$ saturation in a controlled time interval. The plasma cholesterol and red blood cell membrane cholesterol levels were inversely correlated with the percent changes in $O_2$ saturation: $R^2=0.2996$ and $R^2=0.3870$, respectively (FIG. 5).

Conclusions

Again, plasma cholesterol and red blood cell membrane cholesterol levels inversely correlated with the trans-red blood cell-membrane $O_2$ diffusion rate, and high blood cholesterol restricted $O_2$ transport.

Study 3

This study determined that groups of patients with ranges of cholesterol levels can also be grouped by the rate at which oxygen diffuses from their red blood cells.

Materials and Methods

In this third study, red blood cell $O_2$ diffusion was studied as described above in blood from 54 volunteers, whose blood hematocrit was again standardized to 40%. Patients were grouped by plasma cholesterol (mg/dl) of <199 (n=11), 200 to 224 (n=15), 225 to 249 (n=23), and 275 to 299 (n=5).

Results

Figure 6:
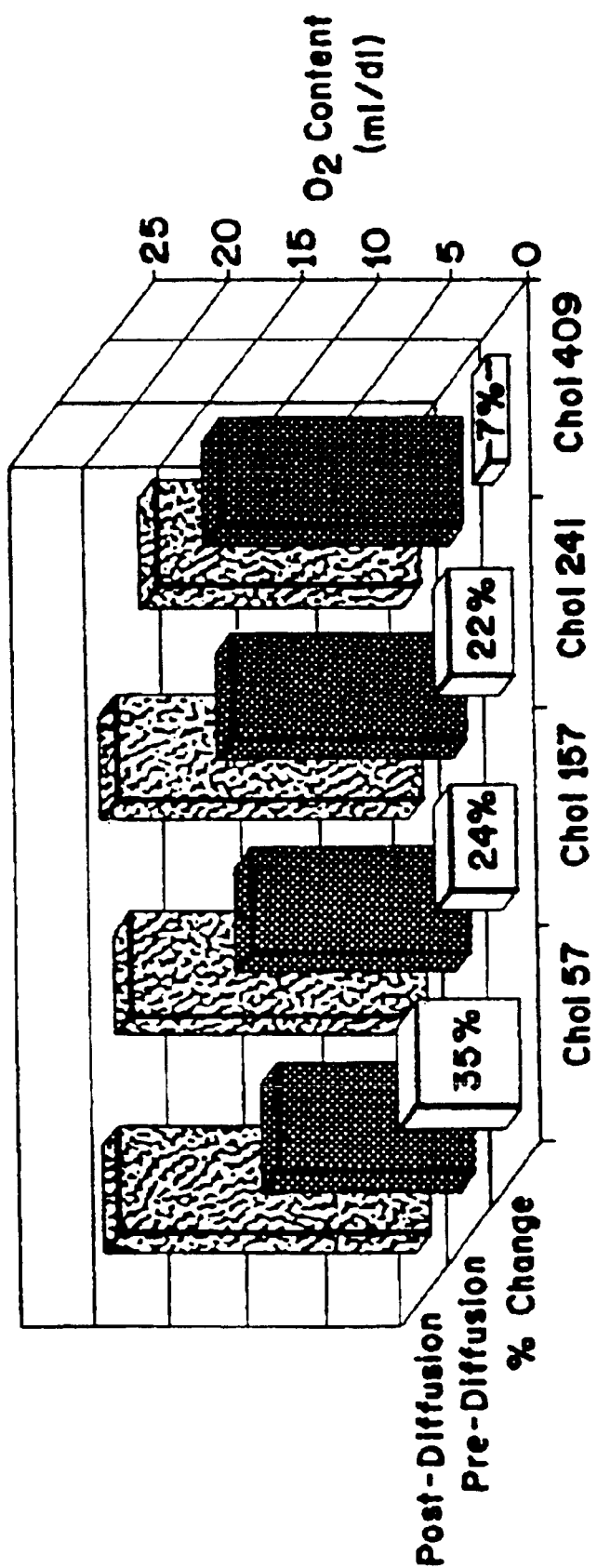
FIG. 6 illustrates that groups of patients with ranges of cholesterol levels can also be grouped by the rate at which oxygen diffuses from their red blood cells

The results of this study are reported in FIG. 6. FIG. 6 illustrates that the 3 plasma cholesterol groups >200 mg/dl all had marked $O_2$ diffusion reductions, compared with the <199 mg/dl group, at 1 min: 82% (p=0.080), 70% (p=0.036), and 100% (p=0.012), respectively; and at 2 min: 32% (p=0.05), 45% (p=0.008), and 66% (p=0.001), respectively. When the hypoxic conditions were maintained over 12 min, the $O_2$ diffusion depravation induced by hypercholesterolemia was cumulative.

Conclusions

This study determined that groups of patients with ranges of cholesterol levels can also be grouped by the rate at which oxygen diffuses from their red blood cells.

Study 4

This study provided an extended analysis of groups of patients with ranges of cholesterol levels and determined short measurement times that revealed different oxygen diffusion rates from red blood cells.

Materials and Methods

This study was an extended analysis involving 93 patents. The patients were grouped into 5 quintiles by plasma cholesterol concentrations: 175 to 199 mg/dl. 200 to 224 mg/dl, 225 to 249 mg/dl, 250 to 274 mg/dl, and 275 to 299 mg/dl.

Results

The 5 cholesterol groups layered out as expected with respect to the percent change in blood $O_2$ diffusion. The greatest percentage change occurred in the lowest cholesterol group; the least percent change in the highest cholesterol group.

Conclusions

A very clear differentiation between these groups could be seen within the first 2 min of circulation in an apparatus according to the invention, the equivalent of about 2 sec of cardiac circulation (FIG. 7).

The invention has been described with reference to various specific and preferred embodiments and techniques. However, it should be understood that many variations and modifications may be made while remaining within the spirit and scope of the invention.

What is claimed is:

1. A method for determining a patient's blood oxygen transport, comprising:

obtaining a blood sample from the patient;

measuring a rate of oxygen diffusion across a membrane of a red blood cell of the blood sample; and correlating the measured rate with:

susceptibility to angina observed in a control population, or in the patient, at the measured rate; and residence time of the blood in the heart during stress.

2. The method of claim 1, wherein the step of measuring comprises:

exposing the red blood cell to oxygen;

exposing the red blood cell to an environment depleted of oxygen; and monitoring either a blood level of oxygen, a level of oxygen bound to hemoglobin, or both.

3. The method of claim 2, wherein exposing the red blood cell to oxygen comprises circulating a blood sample in a closed loop diffusion chamber, the chamber housing an atmosphere comprising oxygen.

4. The method of claim 3, wherein the atmosphere comprising oxygen comprises atmospheric gas pressures.

5. The method of claim 4, wherein the gas pressures comprise about 160 mm Hg $O_2$ and about 4 mm Hg $CO_2$.

6. The method of claim 3, wherein the atmosphere comprising oxygen comprises capillary gas pressures.

7. The method of claim 6, wherein the gas pressures comprise about 23 mm Hg $O_2$ and about 46 mm Hg $CO_2$.

8. The method of claim 3, wherein circulating lasts for about 6 min.

9. The method of claim 2, wherein exposing the red blood cell to an environment depleted of oxygen comprises circulating a blood sample in a closed loop diffusion chamber, the chamber housing an atmosphere comprising nitrogen and depleted of oxygen.

10. The method of claim 9, wherein the atmosphere is supplied from a container of commercial grade nitrogen gas.

11. The method of claim 9, wherein circulating lasts for about 15 min.

12. The method of claim 2, wherein the step of exposing the red blood cell to oxygen precedes the step of exposing the red blood cell to an environment depleted of oxygen.

13. The method of claim 2, wherein the step of exposing the red blood cell to an environment depleted of oxygen precedes the step of exposing the red blood cell to oxygen.

14. The method of claim 1, wherein the measuring step is performed on a whole blood sample comprising anticoagulant.

15. An apparatus for measuring diffusion of oxygen across a red blood cell membrane comprising an oxygen level detector, a gas exchange system, and a red blood cell transport system;

the red blood cell transport system that transports a fluid containing red blood cells through the gas exchange system and the oxygen level detector, the red blood cell transport system comprising:
a) a sample receiving system to take in a sample of a red blood cell;
b) a pump that transports a red blood cell from the sample receiving system to the gas exchange system and the oxygen level detector;

the gas exchange system that couples to a gas source and exchanges a gas with the fluid containing the red blood cells at a rate faster than the rate at which the gas diffuses across a membrane of the red blood cell, the gas exchange system comprising:
a) a housing defining a gas inlet, a gas outlet, and a chamber;
b) a gas permeable tubing at least partially located within the housing for diffusing the gas from the chamber to a red blood cell contained within the gas permeable tubing;

wherein the gas permeable tubing comprises a lumen effective for containing red blood cells; the housing exposing successive sample of red blood cells to the gases without cross-contamination between the samples;

the oxygen level detector that detects oxygen levels in a red blood cell or in fluid surrounding the red blood cell, the oxygen level detector comprising:
a) a light source producing light having an absorption free wavelength;
b) at least one filter;
c) photopickups to detect the transmission of light at the absorption free wavelength; and a control system comprising a microprocessor electronically coupled to the oxygen level detector, the gas exchange system, and the red blood cell transport system to operably derive amounts of oxygen levels in a red blood cell, wherein the sample receiving system and the gas exchange system are present in a modular, cartridge-type insert, the cartridge-type insert being configured to be inserted into the apparatus for connection to the pump, the oxygen level detector and the control system, and removed from the apparatus for disposal.

16. The apparatus of claim 15, wherein the oxygen level detector comprises a spectrophotometric detector.

17. The apparatus of claim 16, further comprising dual spectrophotometric detectors for determination of plasma oxygen and oxygenated hemoglobin.

18. The apparatus of claim 15, wherein the oxygen level detector comprises a fluorometric detector.

19. The apparatus of claim 15, wherein the gas exchange system comprises a closed loop diffusion system; the closed loop diffusion system comprising the gas permeable tubing and the housing.

20. The apparatus of claim 15, wherein the pump of the red blood cell transport system comprises an aspirator.

21. The apparatus of claim 20, wherein the pump is a peristaltic pump.

22. The apparatus of claim 15, wherein the sample receiving system comprises a vacutainer.

23. The apparatus of claim 15, wherein the catridge-type insert reversibly clips to the apparatus.

24. The apparatus of claim 15, wherein the sample receiving system comprises a syringe.

25. The apparatus of claim 15, wherein the gas permeable tubing has a flat shape.

26. The apparatus of claim 15, wherein the gas permeable tubing has a rectangular shape.

27. The apparatus of claim 15, wherein the gas permeable tubing is a removable component of the gas exchange system for disposal of the tubing and red blood cell without contamination of the gas exchange system.

28. The apparatus of claim 15, wherein chamber of the gas exchange system is an environmental chamber having a predetermined oxygen atmosphere concentration within the chamber.

29. The apparatus of claim 28, wherein the oxygen atmosphere concentration increases oxygen diffusion of a red blood cell by about 97.5% in about one minute.

30. The apparatus of claim 28, wherein the oxygen atmosphere concentration is at about 40 mm Hg and decreases oxygen diffusion of a red blood cell by about 75.0%.

31. The apparatus of claim 28, wherein the oxygen atmosphere concentration is at about 20 mm Hg and decreases oxygen diffusion of a red blood cell by about 40.0% in less than 20 minutes.

32. The apparatus of claim 31, wherein the oxygen atmosphere concentration decreases the oxygen diffusion of a red blood cell in less than 2 minutes.

33. The apparatus of claim 15, wherein the light source produces light at a wavelength of at least 358 nm.

34. The apparatus of claim 33, wherein the light source produces light at a wavelength of about 660 nm.

35. The apparatus of claim 33, wherein the light source produce light at a wavelength of about 805 nm.

36. The apparatus of claim 15, wherein the control system comprises a measuring system that measures the amount of diffusion at least once every 15 seconds.

37. The apparatus of claim 36, wherein the control system further comprises a display for displaying the measurements taken by the measuring system of the apparatus.

38. The apparatus of claim 36, wherein the control system further comprises a printer for printing the measurements taken by the measuring system of the apparatus.

39. The apparatus of claim 36, wherein the control system further comprises a data retention apparatus for retaining data measurements taken by the measuring system of the apparatus.

40. A method for determining a patient's susceptibility to angina, comprising:
obtaining a blood sample from the patient;
measuring a rate of oxygen diffusion across a membrane of a red blood cell of the blood sample;
correlating the measured rate with the susceptibility to angina observed in a control population, or in the patient, at the measured rate; and correlating the measured rate with residence time of the blood in the heart during stress.

41. The method of claim 40, wherein the step of measuring comprises:
 exposing the red blood cell to oxygen;
 exposing the red blood cell to an environment depleted of oxygen; and
 monitoring either a blood level of oxygen, a level of oxygen bound to hemoglobin, or both.

42. A method for determining a patient's blood oxygen transport, comprising:
 obtaining a blood sample from the patient;
 measuring a rate of oxygen diffusion across a membrane of a red blood cell of the blood sample; and
 correlating the measured rate with established levels of blood lipid to determine the patient's relative or absolute blood lipid level; and
 further comprising comparing the patient's lipid level to the patient's previous lipid level measured at an earlier time to determine the patient's blood oxygen transport.

* * * * *

UNITED STATES PATENT AND TRADEMARK OFFICE
CERTIFICATE OF CORRECTION

PATENT NO. : 6,806,091 B1
DATED : October 19, 2004
INVENTOR(S) : Buchwald et al.

It is certified that error appears in the above-identified patent and that said Letters Patent is hereby corrected as shown below:

Title page,
Item [56], References Cited, OTHER PUBLICATIONS, "Anderson, H.V., et al." reference, "monitoring coronary interventions," should read -- monitoring following coronary interventions, --
"Di Mario, C. et al." reference, 16:53-59." should read -- 16:53-59 (1995). --

Column 1,
Line 43, "concentration gradients, there is" should read -- concentration gradients; there is --

Column 3,
Line 39, "angina pectoris, The" should read -- angina pectoris. The --
Line 47, "plasma and" should read -- plasma, and --

Column 5,
Line 13, "affect P02 values" should read -- affect $P_{02}$ values --

Column 6,
Line 64, "0.4 to 1.0 sec. (1,5,6)." should read -- 0.4 to 1.0 sec (1,5,6). --

Column 8,
Line 50, "$10^{-1}$ $sec^{-1}$" should read -- $10^{-2}$ $sec^{-1}$ --

Column 9,
Line 23, "[1]" should read -- [1] --
       $V_t$                $V_1$ Column 10,
Lines 8 and 21, "$10^{-1}$" should read -- $10^{-3}$ --
Line 27, "$10^{-1}$" should read -- $10^{-4}$ --

Column 11,
Line 23, "system 17 Typically" should read -- system 17. Typically --

Column 12,
Line 67, "system 17 Gas" should read -- system 17. Gas --

UNITED STATES PATENT AND TRADEMARK OFFICE
CERTIFICATE OF CORRECTION

PATENT NO. : 6,806,091 B1
DATED : October 19, 2004
INVENTOR(S) : Buchwald et al.

It is certified that error appears in the above-identified patent and that said Letters Patent is hereby corrected as shown below:

Column 13,
Line 25, "tubing 23 and outflow" should read -- tubing 23, and outflow --
Line 34, "blood cell/transport system" should read -- blood cell transport system --

Column 18,
Line 52, "one aliquol of" should read -- one aliquot of --

Signed and Sealed this

Thirty-first Day of May, 2005

JON W. DUDAS
*Director of the United States Patent and Trademark Office*